(12) United States Patent
Li

(10) Patent No.: US 7,461,961 B2
(45) Date of Patent: Dec. 9, 2008

(54) FIBER OPTIC DARKFIELD RING LIGHT

(75) Inventor: Falai Li, Eden Prairie, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 11/740,569

(22) Filed: Apr. 26, 2007

(65) Prior Publication Data

US 2007/0201020 A1    Aug. 30, 2007

Related U.S. Application Data

(63) Continuation of application No. 10/888,302, filed on Jul. 9, 2004, now Pat. No. 7,220,034.

(60) Provisional application No. 60/486,502, filed on Jul. 11, 2003.

(51) Int. Cl.
    *F21V 7/04* (2006.01)
(52) U.S. Cl. .................... 362/554; 362/33; 362/575
(58) Field of Classification Search ................. 362/551, 362/554–555, 575, 33; 359/385; 365/237, 365/239
    See application file for complete search history.

(56) References Cited

U.S. PATENT DOCUMENTS

| | | | |
|---|---|---|---|
| 4,328,553 A | 5/1982 | Fredriksen et al. | |
| 4,464,705 A | 8/1984 | Horowitz | |
| 4,644,172 A | 2/1987 | Sandland et al. | |
| 4,823,394 A | 4/1989 | Berkin et al. | |
| 5,091,963 A | 2/1992 | Litt et al. | |
| 5,153,668 A | 10/1992 | Katzir et al. | |
| 5,497,381 A | 3/1996 | O'Donoghue et al. | |
| 5,592,295 A | 1/1997 | Stanton et al. | |
| 5,640,200 A | 6/1997 | Michael | |
| 5,641,960 A | 6/1997 | Okubo et al. | |
| 5,787,190 A | 7/1998 | Peng et al. | |
| 5,822,055 A | 10/1998 | Tsai et al. | |
| 5,850,466 A | 12/1998 | Schott | |
| 5,856,844 A | 1/1999 | Batterman et al. | |
| 5,917,588 A | 6/1999 | Addiego | |
| 5,949,901 A | 9/1999 | Nichani et al. | |
| 6,137,303 A | 10/2000 | Deckert et al. | |
| 6,140,254 A | 10/2000 | Endisch et al. | |
| 6,147,357 A | 11/2000 | Nicolesco | |
| 6,153,361 A | 11/2000 | Liu et al. | |
| 6,290,382 B1 | 9/2001 | Bourn et al. | |
| 6,314,379 B1 | 11/2001 | Hu et al. | |
| 6,324,298 B1 | 11/2001 | O'Dell et al. | |
| 6,412,326 B1 | 7/2002 | Hubbard et al. | |
| 6,565,920 B1 | 5/2003 | Endisch | |
| 6,640,151 B1 | 10/2003 | Somekh et al. | |
| 6,708,074 B1 | 3/2004 | Chi | |
| 6,832,849 B2 | 12/2004 | Yoneda et al. | |
| 2003/0030050 A1 | 2/2003 | Choi | |
| 2003/0202178 A1 | 10/2003 | Tsuji et al. | |

*Primary Examiner*—Ali Alavi
(74) *Attorney, Agent, or Firm*—Dicke, Billig & Czaja, PLLC

(57) ABSTRACT

A fiber optic darkfield ring light with many angled fiber optic light lines with direct illumination in a very small package. The fiber optic darkfield ring light includes a base with multiple light heads and multiple light covers attached thereto, a main cover, an optional cord grip, and an optional hood. It incorporates multiple fiber optic line arrays positioned at low angle and used in conjunction with a strobe light source.

17 Claims, 4 Drawing Sheets

FIBER OPTIC DARKFIELD RING LIGHT

CROSS-REFERENCE TO RELATED APPLICATION

This application is a continuation of U.S. Non-Provisional patent application Ser. No. 10/888,302, filed on Jul. 9, 2004, now U.S. Pat. No. 7,220,034 and entitled "Fiber Optic Darkfield Ring Light", which claims the benefit of U.S. Provisional Patent Application No. 60/486,502, filed on Jul. 11, 2003, and entitled Fiber Optic Darkfield Ring Light.

BACKGROUND OF THE INVENTION

1. Technical Field

The present invention relates to dark field illumination as is widely used in machine vision to detect features higher or lower than regular surfaces.

2. Background Information

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics, and more particularly, faster, more advanced computers and electronics whether it be on an assembly line, on test equipment in a lab, on the personal computer at one's desk, or in the home electronics and toys.

The manufacturers of semiconductors have made vast improvements in end product quality, speed and performance as well as in manufacturing process quality, speed and performance. However, there continues to be demand for faster, more reliable and higher performing semiconductors.

Processors who are building semiconductors and like microelectronics must be able to provide ample illumination for the machine vision process. Users of inspection equipment continue to demand smaller, more intense, more robust illumination.

In the past, it was typical to use halogen, laser or other illumination methods rather than fiber optic. Where fiber optic has been tried, the setup has typically involved using a metal ring with a polished surface attached to standard fiber optic ring light to achieve some dark field illumination.

SUMMARY

An illuminator including a base with multiple light heads attached thereto, and fiber optics provided in each of the multiple heads.

BRIEF DESCRIPTION OF THE DRAWINGS

Preferred embodiment of the invention, illustrative of the best mode in which applicant has contemplated applying the principles, are set forth in the following description and are shown in the drawings and are particularly and distinctly pointed out and set forth in the appended claims. Similar numerals refer to similar parts throughout the drawings.

DETAILED DESCRIPTION

Figure 1:
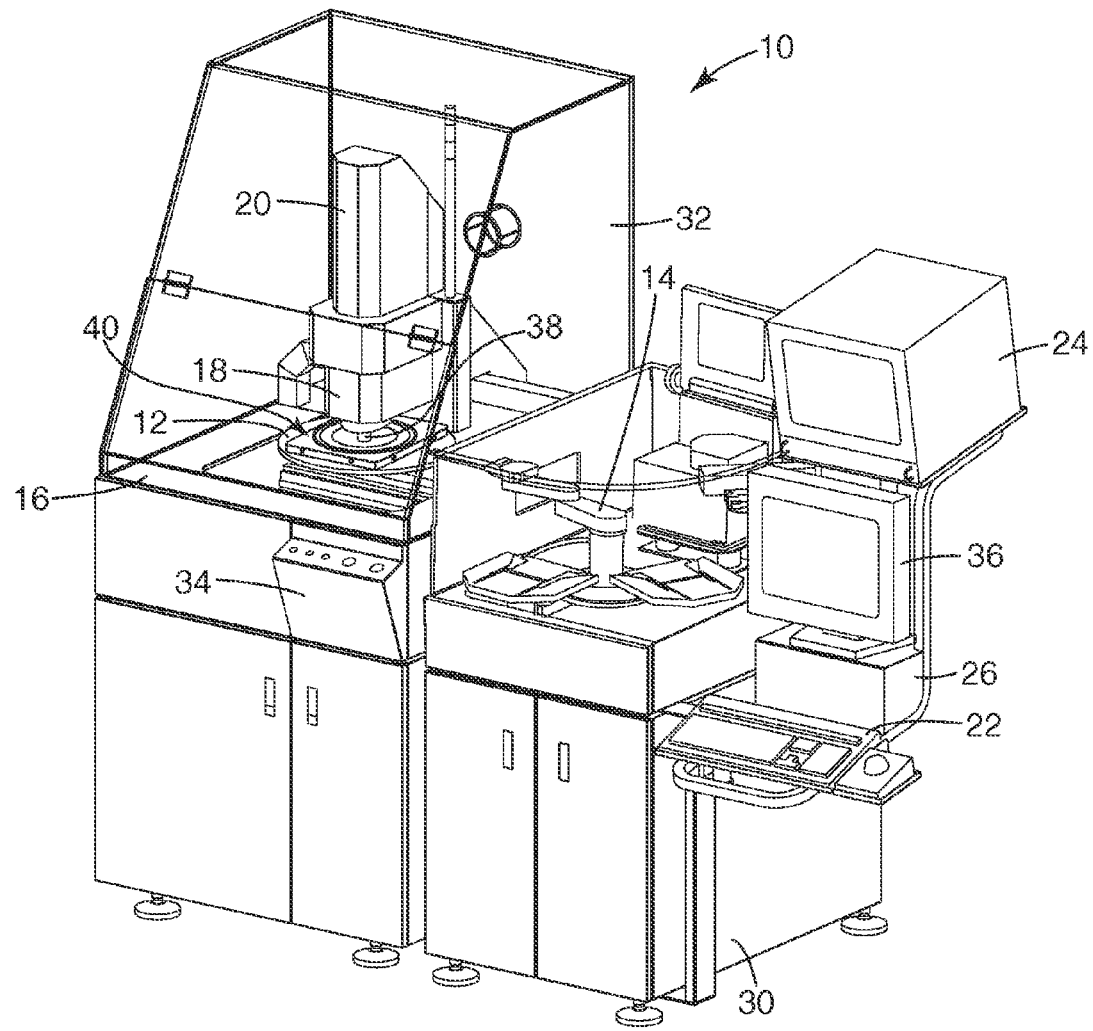
FIG. 1 is a diagram illustrating an automated defect inspection system according to one embodiment of the present invention.

FIG. 1 is a diagram illustrating an automated defect inspection system 10 according to one embodiment of the present invention. System 10 is used in one environment to find defects on die on patterned wafers, but is intended for this and other uses including for inspecting whole wafers, sawn wafers, broken wafers, wafers of any kind on film frames, die in gel paks, die in waffle paks, MCMs, JEDEC trays, Auer boats, and other wafer and die package configurations (although hereinafter all of these uses shall be referred to generally as inspection of wafers or substrates).

System 10 includes a wafer test plate 12, means for providing a wafer to the test plate referred to as 14, a wafer alignment device 16 for aligning each and every wafer at the same x, y, and θ location or x, y, z, and θ location, a focusing mechanism 18, a camera 20 or other visual inspection device for visual inputting of good die during training and for visual inspection of other unknown quality die during inspection, a parameter input device 22 for inputting parameters and other constraints or information such as sensitivity parameters, geometries, die size, die shape, die pitch, number of rows, number of columns, etc., a display 24 for displaying the view being seen by the camera presently or at any previously saved period, a computer system 26 or other computer-like device having processing and memory capabilities for saving the inputted good die, developing a model therefrom, and comparing or analyzing other die in comparison to the model, a frame 30, a hood 32, a control panel 34, a system parameters display 36, objective 38, and a fiber optic darkfield ring light 40.

The means for providing a wafer to the test plate referred to as 14 may be either manual in that the user moves the wafer from a cassette or magazine to the test plate 12, or automatic as is shown in the embodiment of FIG. 1. In the automatic environment, the wafer providing means 14 includes a robotic arm that pivots from a first position where a wafer is initially grasped from a magazine or cassette to a second position where the wafer is positioned on the wafer test plate 12 for inspection. After inspection, the robotic arm pivots the wafer from the second position at the test plate 12 back to the first position where the wafer is placed back in or on the magazine or cassette.

In one form of the invention, system 10 is trained as to what a "good die" comprises by aligning via device 16 and viewing via camera 20 a plurality of known good die and forming a model within computer system 26 to define what an ideal die should look like based upon the common characteristics viewed. In one embodiment, after being trained, system 10 is used to inspect die of unknown quality. During inspection according to one embodiment, system 10 collects an image of a wafer using the camera 20 by moving the plate 12 to align the camera with a first die or other portion thereof, viewing and recording that die or portion thereof by opening the shutter and allowing the camera to view and record the image, moving the plate 12 to align the camera with a second die or portion thereof, viewing and recording the second die or portion thereof, and repeating these steps until all of the die or portions thereof on the wafer that are desired to be viewed have been viewed and recorded. In one embodiment, system 10 determines where defects are located on a given die being viewed based upon the "good die" model.

In another embodiment, rather than using a stop and go procedure to capture images of die on the wafer, system 10 collects an image of the wafer using the camera 20 by continuously moving the plate 12 so as to scan over all of the die on the wafer, whereby the wafer is illuminated by a strobe light at a sequence correlating to the speed of the moving plate so that each die is strobed at the precise time it is under the camera 20. This allows for the continuous collecting of images without necessitating the stop and go procedure of aligning the camera with a first die, viewing and recording that die, moving the plate 12 to align the camera with a second die, viewing and recording this second die, and repeating these steps until all of the die on the wafer have been viewed and recorded, etc.

In one embodiment, fiber optic darkfield ring light 40 is mounted between two millimeters and five millimeters above test plate 12. Substrates to be inspected are placed through an inspection region 94 (shown in FIG. 2) of ring light 40, and rest on test plate 12. Ring light 40 provides darkfield illumination to substrates as described in further detail below with reference to FIGS. 2-6.

Figure 2:
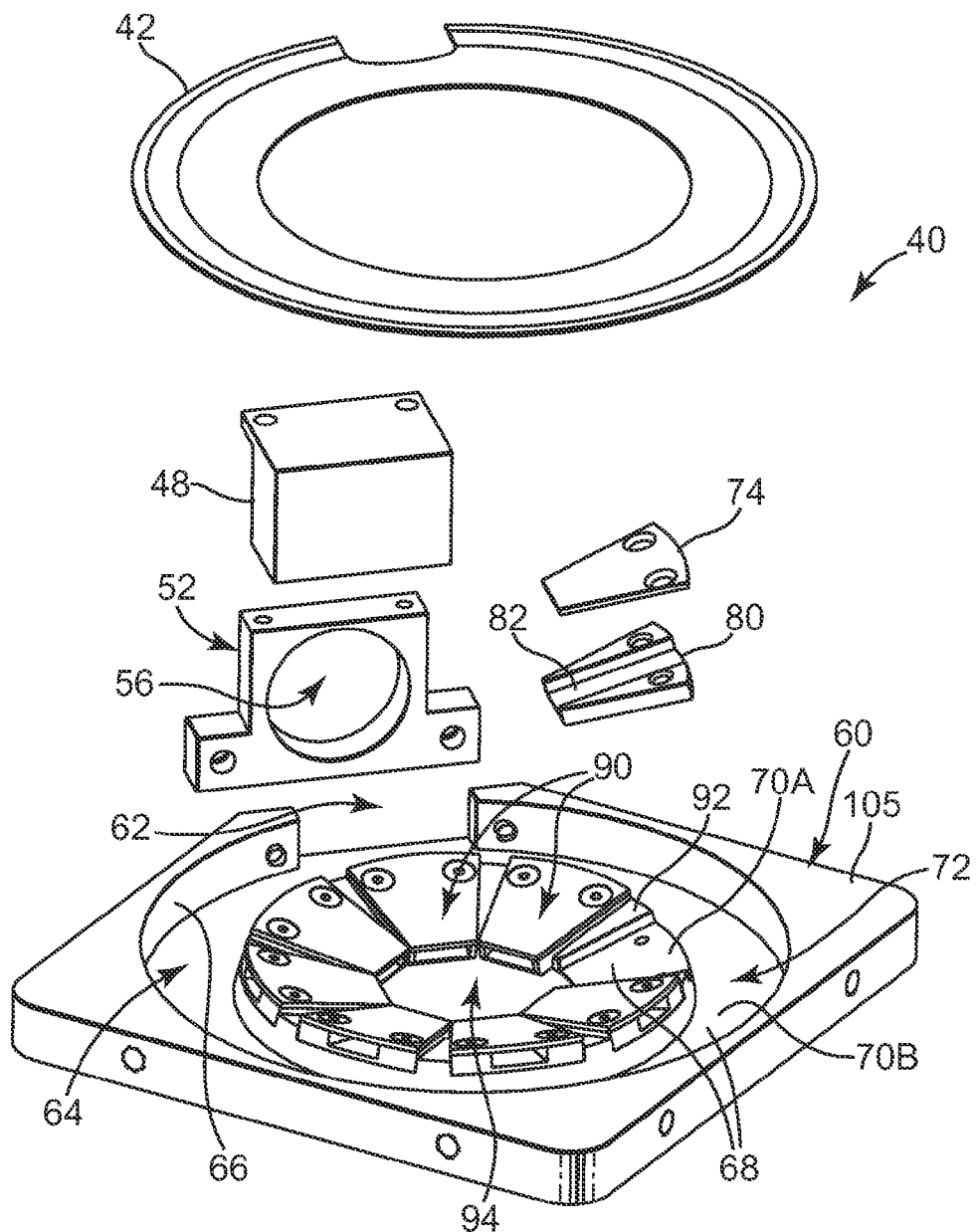
FIG. 2 is a diagram illustrating a perspective view of one embodiment of a fiber optic darkfield ring light in a partially assembled state.

The fiber optic darkfield ring light 40 of the present invention is shown in FIG. 2, and in general consists of many angled fiber optic light lines with direct illumination in a very small package that is at least ⅕ of the thickness of other known ring light systems. Ring light 40 according to one embodiment provides very intense dark field illumination and is sized so as to be capable of use with multiple objectives in an inspection system. This unique design enables new inspection capabilities including nodules, craters, particles and other surface defects. It also enables inspection of very dark wafers in bright field due to wafer micro-roughness.

Figure 3:
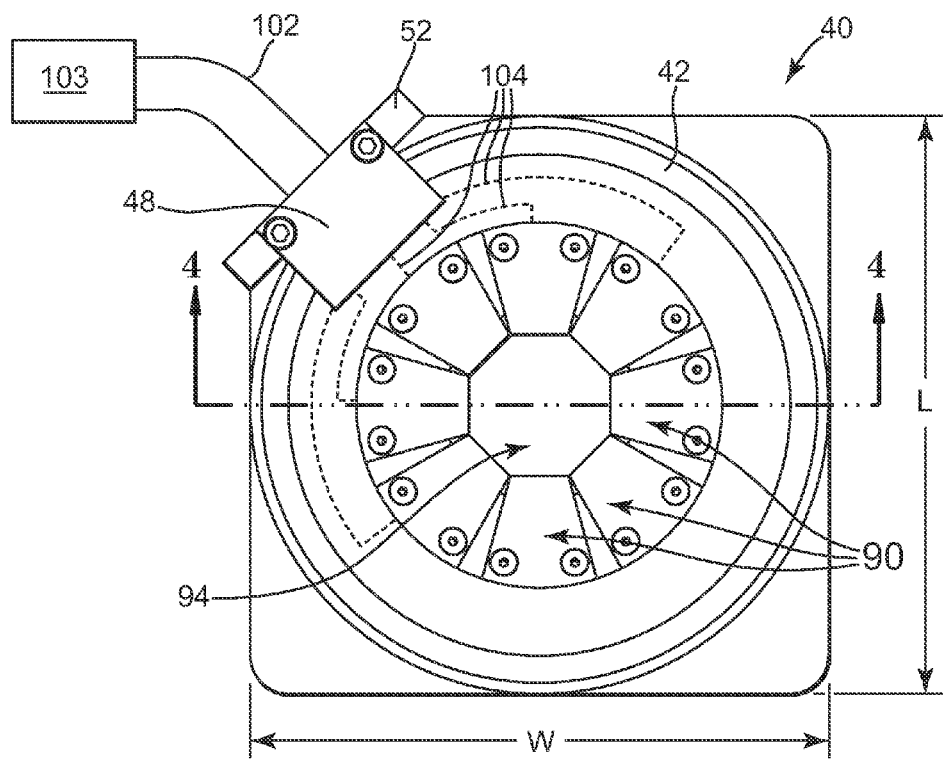
FIG. 3 is a diagram illustrating a top view of the fiber optic darkfield ring light shown in FIG. 2 in an assembled state according to one embodiment of the present invention.
Figure 6:
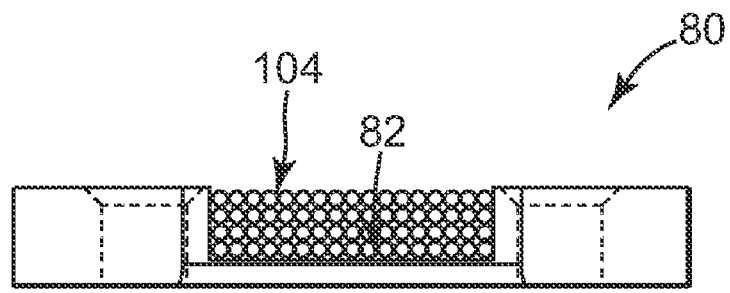
FIG. 6 is a diagram illustrating a front view of the light head shown in FIG. 5 according to one embodiment of the present invention.

In more detail, the fiber optic darkfield ring light 40 as shown in FIG. 2 includes a base 60 with multiple light heads 80 attached thereto (with one removed and pointed out as 80) and multiple light covers 74 attached thereto (with one removed and pointed out as 74), a main cover 42, an optional cord grip 52, and an optional hood 48. The fiber optic darkfield ring light 40 in the embodiment shown has eight (8) fiber optic line arrays 90 (where each line array 90 includes a light head 80, a light cover 74 and fiber optics that are shown in FIGS. 3 and 6) positioned at a low angle (15 degrees for the embodiment shown). In one embodiment, the system 40 is used in conjunction with a strobe light source.

The base 60 provides a mounting surface for the multiple fiber optic line arrays 90. In the embodiment shown, the base 60 provides a mounting surface for eight (8) fiber optic line arrays 90. The base 60 in more detail is a block with a top base surface 105 and a recessed area 64 therein having a first surface portion 70A on which the light heads 80 are mounted. The recessed area 64 is generally cylindrical in shape, and is defined by a wall 66 and a bottom recess surface 68. The bottom recess surface 68 includes the first surface portion 70A on which the light heads 80 are mounted, and a second surface portion 70B extending outward from and surrounding the first surface portion 70A. In the illustrated embodiment, surface portions 70A and 70B are ring-shaped. In the embodiment shown, the mounted heads 80 have an inward taper and are positioned in a generally circular manner around an inspection region 94. A fiber optic routing channel 72 is defined behind the light heads 80 and appears as an annual ring area. The surface 70A in the recessed area 64 on which the light heads 80 are mounted is designed in one embodiment in a polygonal fashion, in the embodiment shown an octogonal pattern with eight notches 92 extending upward from surface 70A for eight (8) fiber optic line arrays 90, to simulate a true circular ring. A cutout notch 62 from the routing channel 72 is notched out of the base 60, thereby providing a lateral access into the recessed area 64.

Each light head 80 includes a channel 82 formed therein that provides room for an individual set or group of fiber optic lines for each fiber optic line array 90 (as shown in FIG. 6). Each light cover 74 provides a cover for an individual set or group of fiber optic lines for each fiber optic line array 90. The main cover 42 or multi-head cover protects the fiber optics once assembled by covering the routing channel 72.

The cord grip 52 provides a transition for all fiber optics from eight (8) fiber optic line arrays 90 to one (1) fiber optic input bundle that is placed within the cord grip 52 positioned at the cut-out notch 62 (and attachable there). The fiber optic input bundle is positioned within a circular hole 56 in cord grip 52. The hood 48 provides protection for fiber optics in the transition into the unit 40 and also may assist in securing the fiber optics in place.

Assembly of the fiber optic darkfield ring light 40 occurs as follows in one embodiment: Assemble multiple fiber optic line arrays 90 where each line array 90 includes a light head 80, a light cover 74 and fiber optics (shown in FIGS. 3 and 6). Route all fiber optics through hole 56 of the cord grip 52. Position and secure the main cover 42 and position and secure the hood 48.

FIG. 3 is a diagram illustrating a top view of the fiber optic darkfield ring light 40 shown in FIG. 2 in an assembled state according to one embodiment of the present invention. As shown in FIG. 3, a first end of a fiber optic input bundle 102 is positioned within cord grip 52 of ring light 40. In one embodiment, the fiber optic bundle 102 includes hundreds of individual fiber optic lines. In one embodiment, the fiber optic lines in bundle 102 are separated in the routing channel 72 (FIG. 2) into eight groups or sets 104 of fiber optic lines. Only five sets 104 of fiber optic lines are shown in FIG. 3 to simplify the illustration. In one embodiment, each set 104 of fiber optic lines includes a plurality of fiber optic lines. Each set 104 of fiber optic lines is routed through the routing channel 72 (FIG. 2) to one of the line arrays 90. The sets 104 of fiber optic lines are represented in FIG. 3 by hidden lines, since the fiber optic lines are covered by main cover 42.

As shown in FIG. 3, fiber optic darkfield ring light 40 has a length, L, and a width, W. In one embodiment, L and W are each 3.75 inches. The length and width of ring light 40 depend upon the size of objects to be illuminated. In other embodiments, ring light has a length and/or width that are greater or less than 3.75 inches.

In use, the ring light system 40 uses fiber optics 104 to deliver light from a light source 103 (such as a strobing light source) to the area to be inspected in the inspection region 94, which is at the center of the substantially circular arrangement of line arrays 90. In one embodiment, light source 103 provides light that is directed by fiber optic input bundle 102 to ring light 40. The light is then directed by each set 104 of fiber optic lines to corresponding ones of the line arrays 90, which direct the light to inspection region 94. In one form of the invention, light source 103 strobes to provide short flashes of light that are correlated with a velocity or position of a substrate being inspected. The multiple (in the embodiment shown eight) fiber optic line arrays 90 deliver intense light in a very small profile, and at a low angle (such as 15 degrees)

from the fiber optic line arrays 90 to the inspection surface. This angle is determined by the angle of the mounting surface portion 70A (FIG. 2) on the base 60, as will be described in further detail below with reference to FIG. 4.

Figure 4:
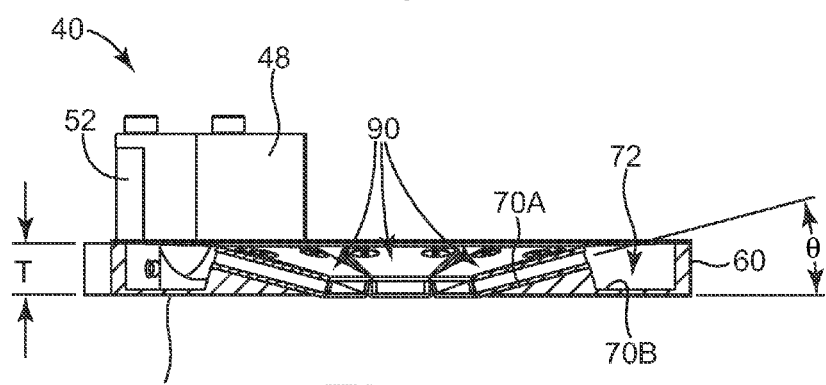
FIG. 4 is a diagram illustrating a cross-sectional view of the fiber optic darkfield ring light along section lines 4-4 in FIG. 3 according to one embodiment of the present invention.

FIG. 4 is a diagram illustrating a cross-sectional view of the fiber optic darkfield ring light 40 along section lines 4-4 in FIG. 3 according to one embodiment of the present invention. Surface 70A of base 60 is at an angle, θ, with respect to a bottom base surface 106 of ring light 40. The bottom base surface 106 of ring light 40 defines a horizontal plane (perpendicular to the paper in FIG. 4) that is parallel to the surface to be inspected). Since line arrays 90 are mounted on the angled surface 70A, line arrays 90 are also at an angle, θ, with respect to the bottom base surface 106 of ring light 40, and with respect to the surface to be inspected. Thus, line arrays 90 deliver light at an angle, θ, to an object placed in the inspection region 94. In one embodiment, the angle, θ, is 15 degrees. In other embodiments, the angle, θ, is in the range of 5 to 25 degrees. In the illustrated embodiment, surface portion 70B is parallel to the bottom base surface 106 and the surface to be inspected.

As shown in FIG. 4, base 60 has a height or thickness, T. In one embodiment, T is less than about 0.5 inches. In one form of the invention, T is equal to 0.35 inches. With a thickness of only 0.35 inches in one embodiment, ring light 40 is sized so as to be capable of use with multiple objectives in an inspection system. The objectives in inspection systems are typically mounted on a rotating turret. The low profile of ring light 40 allows the different objectives to be rotated into position without the interference that would be caused by a higher profile lighting system.

Figure 5:
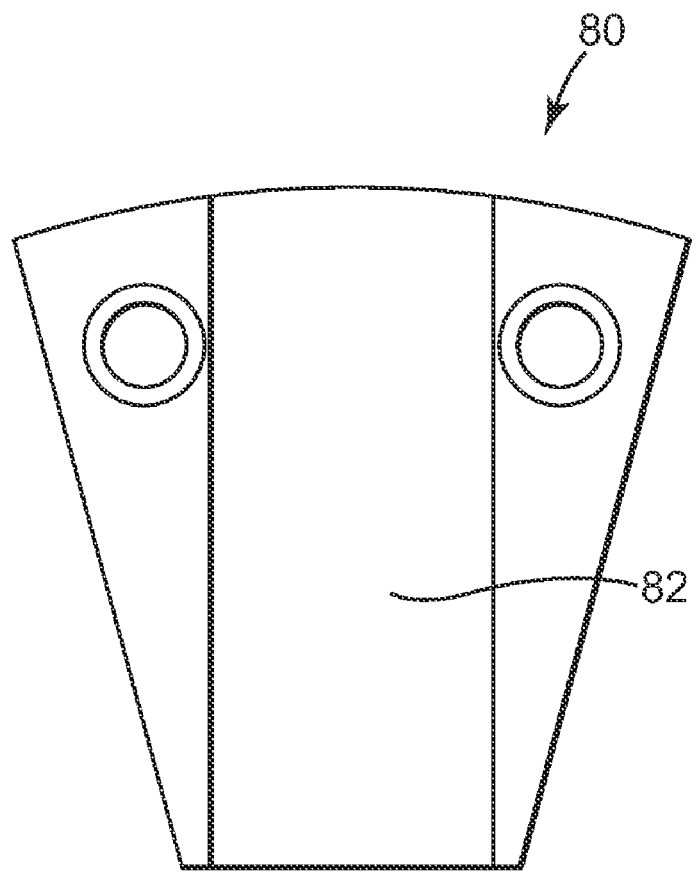
FIG. 5 is a diagram illustrating a top view of a light head according to one embodiment of the present invention.

FIG. 5 is a diagram illustrating a top view of one of the light heads 80 of ring light 40 according to one embodiment of the present invention. As shown in FIG. 5, light head 80 is tapered such that the width of the light head 80 becomes narrower moving from the back of the light head 80 (at the top of FIG. 5) to the front of the light head 80 (at the bottom of FIG. 5). Channel 82 is formed in light head 80. A set 104 of fiber optic lines from fiber optic bundle 102 (FIG. 3) is routed through the back of the light head 80 to the front of the light head 80, and directs light out of the front of the light head 80.

FIG. 6 is a diagram illustrating a front view of the light head 80 shown in FIG. 5 according to one embodiment of the present invention. As shown in FIG. 6, a set 104 of fiber optic lines are positioned in the channel 82 of the light head 80. In one embodiment, the fiber optic lines in each light head 80 are configured in a light line configuration, so that each line array 90 outputs a horizontal line of light. In the light line configuration according to one form of the invention, the set 104 of fiber optic lines for each light head 80 is in the form of a fiber optic bundle with a relatively flat, rectangular shape, such as shown in FIG. 6. In effect, each fiber optic line array 90 converts a point source to a line of light, and this design provides for multiple, such as 8-lines at a low angle (15 degrees for the illustrated embodiment) to create a very low profile, intense dark field ring light 40.

The unique fiber optic darkfield ring light system 40 according to one embodiment provides intense dark field illumination to highlight features that are higher or lower in height than a regular surface. Examples of such features are nodule and crater defects on the bump top of gold bumped wafers, particles and scratches on surface, etc. The system 40 can be used alone or with other bright field illumination. The system 40 is of much smaller profile compared to off-the-shelf products to provide maximum flexibility with current optics.

In sum, the system 40 is a fiber optic darkfield ring light for illumination. One application is darkfield illumination for use in defect inspection on semiconductors and microelectronics where it illuminates to assist in inspection for defects. One type of defect that it is useful in finding is nodules and craters. It is also very useful for defect detection on gold bump wafers and others wafers with flat bump top. This system is also useful for assisting in defect detection for surface defect detection such as on any relatively flat surface. Overall, it provides for a very low profile, intense dark field ring light 40 for general machine vision and the microscopy industry.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

What is claimed is:

1. A darkfield illuminator, comprising:
   a base;
   a plurality of separate and distinct light heads attached to the base;
   a plurality of fiber optic lines; and
   wherein each of the light heads is configured to hold a plurality of the fiber optic lines and provide darkfield illumination.

2. The darlfield illuminator of claim 1, wherein the base includes a recess formed therein.

3. The darkfield illuminator of claim 2, wherein the recess is substantially cylindrical in shape.

4. The darkfield illuminator of claim 2, wherein the recess is defined by a bottom recess surface and a wall substantially surrounding the bottom recess surface.

5. The darkfield illuminator of claim 4, wherein the bottom recess surface includes a first surface portion that is angled with respect to a surface to be illuminated.

6. The darkfield illuminator of claim 5, wherein the light heads are attached to the first surface portion in a substantially circular arrangement, and are configured to provide light from the fiber optic lines toward a center of the substantially circular arrangement.

7. The darkfield illuminator of claim 1, wherein the plurality of light heads includes at least eight light heads.

8. The darkfield illuminator of claim 1, wherein the plurality of fiber optic lines held by each of the light heads includes a plurality of fiber optic lines that are arranged in a light line configuration, such that the plurality of light heads provides a corresponding plurality of lines of light.

9. The darkfield illuminator of claim 1, wherein the base is less than about one-half inch in height.

10. The darkfield illuminator of claim 1, wherein the base is about 0.35 inches in height.

11. An automated inspection system for inspecting a substrate, comprising:
- a darkfield illumination device for illuminating the substrate with darkfield illumination, the darkfield illumination device including a base having a recess formed therein, the base including a bottom surface at a bottom of the recess, the bottom surface including a first surface portion that is angled with respect to a surface to be illuminated, the darkfield illumination device including a plurality of light heads attached to the first surface portion in a substantially circular arrangement, the light heads each including a plurality of fiber optic lines for providing light toward a center of the substantially circular arrangement at an angle corresponding to the angle of the first surface portion;
- a substrate provider for providing the substrate within the substantially circular arrangement of light heads;
- a visual inspection device for capturing images of the substrate provided by the substrate provider; and
- a controller for identifying defects in the substrate based on the captured images.

12. The automated inspection system of claim 11, wherein the recess is substantially cylindrical in shape.

13. The automated inspection system of claim 11, wherein the plurality of light heads includes at least eight light heads.

14. The automated inspection system of claim 11, wherein the plurality of fiber optic lines in each of the light heads are arranged in a light line configuration, such that the plurality of light heads provide a corresponding plurality of lines of light.

15. The automated inspection system of claim 11, wherein the darkfield illumination device is configured to strobe based on a velocity of the substrate.

16. A method of providing darkfield illumination, the method comprising:
- providing a base having a recess formed therein, the recess defined by a bottom surface and a wall substantially surrounding the bottom surface, the bottom surface including a first surface portion that is angled with respect to a surface to be illuminated;
- attaching a plurality of light heads to the first surface portion in a substantially circular arrangement, the light heads each including a plurality of fiber optic lines; and
- transmitting light through the fiber optic lines of each light head, thereby providing darkfield light toward a center of the substantially circular arrangement at an angle corresponding to the angle of the first surface portion.

17. An illuminator comprising:
- a base with multiple separate and distinct light heads attached thereto; and
- a plurality of fiber optics lines provided in each of the multiple heads for providing darkfield illumination.

* * * * *

UNITED STATES PATENT AND TRADEMARK OFFICE
CERTIFICATE OF CORRECTION

| | |
|---|---|
| PATENT NO. | : 7,461,961 B2 |
| APPLICATION NO. | : 11/740569 |
| DATED | : December 9, 2008 |
| INVENTOR(S) | : Falai Li |

It is certified that error appears in the above-identified patent and that said Letters Patent is hereby corrected as shown below:

Column 6, line 42, please delete "darlfield" and insert --darkfield-- therefor.

Signed and Sealed this

Seventeenth Day of February, 2009

JOHN DOLL
*Acting Director of the United States Patent and Trademark Office*